(12) United States Patent
Meng et al.

(10) Patent No.: US 9,962,109 B2
(45) Date of Patent: May 8, 2018

(54) PERSONAL SPIROMETER

(71) Applicant: PMD HEALTHCARE, Allentown, PA (US)

(72) Inventors: Wayne Meng, Fogelsville, PA (US); Jay Boyce, Colmar, PA (US); Antonio Boyer, Macungie, PA (US)

(73) Assignee: PMD Healthcare, Allentown, PA (US)

( * ) Notice: Subject to any disclaimer, the term of this patent is extended or adjusted under 35 U.S.C. 154(b) by 0 days. days.

(21) Appl. No.: 14/877,390

(22) Filed: Oct. 7, 2015

(65) Prior Publication Data

US 2016/0058325 A1  Mar. 3, 2016

Related U.S. Application Data

(63) Continuation of application No. 12/844,980, filed on Jul. 28, 2010, now abandoned.

(51) Int. Cl.
*A61B 5/091* (2006.01)
*A61B 5/087* (2006.01)
(Continued)

(52) U.S. Cl.
CPC .............. *A61B 5/091* (2013.01); *A61B 5/087* (2013.01); *A61B 5/09* (2013.01); *A61B 5/682* (2013.01);
(Continued)

(58) Field of Classification Search
CPC ....... A61B 5/091; A61B 5/682; A61B 5/7475; A61B 5/7405; A61B 5/7278;
(Continued)

(56) References Cited

U.S. PATENT DOCUMENTS 2,999,495 A * 9/1961 Shipley ................ A61B 5/0935
346/17
3,555,555 A * 1/1971 Lambert .............. A61B 5/0803
324/97

(Continued)

FOREIGN PATENT DOCUMENTS

| CN | 101426424 A | * | 5/2009 | ............. A61B 5/087 |
| EP | 0196396 A1 | * | 10/1986 | ........... A61B 5/0002 |
| JP | 2000298044 A | * | 10/2000 | ............... A61B 5/09 |

OTHER PUBLICATIONS

Miller, M.R. et al., "Standardisation of Spirometry," Eur. Respir. J., vol. 26(2), pp. 319-338, 2005.

*Primary Examiner* — Meredith Weare

(57) ABSTRACT

A portable hand-held spirometer is disclosed for use in taking respiratory tests and storing and displaying test results. The configuration of the spirometer includes handgrips that are positioned to ensure that the user is properly positioned to provide maximum breathing required for valid test results to be obtained. The spirometer also includes a progressively illuminated indicator that can be viewed by the user during a test to provide an indication in real-time to the user of the expected/desired duration of the exhalation or inhalation test. The indicator is completely illuminated only when the measured accumulated volume of air passing through the spirometer equals a predicted volume determined based on the age, gender, height, weight and ethnicity of the user stored in the spirometer. The structures and arrangement of a turbine assembly and sensors is also disclosed. Further, a method of receiving, storing and displaying information on the spirometer via a color touch screen display is also disclosed.

20 Claims, 7 Drawing Sheets

(51) Int. Cl.
*A61B 5/09* (2006.01)
*A61B 5/00* (2006.01)

(52) U.S. Cl.
CPC .......... *A61B 5/7278* (2013.01); *A61B 5/7405* (2013.01); *A61B 5/7435* (2013.01); *A61B 5/7475* (2013.01); *A61B 5/0871* (2013.01); *A61B 2562/16* (2013.01)

(58) Field of Classification Search
CPC ..... A61B 5/7435; A61B 5/09; A61B 2562/16; A61B 5/087; A61B 5/093; A61B 5/0935; A61B 5/095
See application file for complete search history.

(56) References Cited

U.S. PATENT DOCUMENTS

| | | | |
|---|---|---|---|
| 3,680,378 A * | 8/1972 | Aurilio | G01F 1/103 73/861.77 |
| 3,896,792 A * | 7/1975 | Vail | A61B 5/0436 600/532 |
| 4,122,842 A | 10/1978 | Pikul | |
| 4,271,701 A * | 6/1981 | Dempster | G01F 1/38 600/538 |
| 4,299,236 A | 11/1981 | Poirier | |
| 4,495,944 A | 1/1985 | Brisson et al. | |
| 4,635,647 A | 1/1987 | Choksi | |
| 4,658,832 A * | 4/1987 | Brugnoli | A61B 5/0002 340/870.09 |
| 4,736,750 A | 4/1988 | Valdespino et al. | |
| 4,991,591 A | 2/1991 | Jones et al. | |
| D339,635 S | 9/1993 | Waterson et al. | |
| 5,277,195 A | 1/1994 | Williams | |
| 5,518,002 A | 5/1996 | Wolf et al. | |
| 5,715,831 A | 2/1998 | Johnson | |
| 5,816,246 A | 10/1998 | Mirza | |
| 6,019,731 A | 2/2000 | Harbrecht et al. | |
| 6,042,551 A | 3/2000 | Harbrecht et al. | |
| 6,113,549 A | 9/2000 | Johnson | |
| 6,176,833 B1 | 1/2001 | Thomson | |
| 6,238,353 B1 | 5/2001 | Weinstein et al. | |
| 6,447,459 B1 | 9/2002 | Larom | |
| 6,656,129 B2 | 12/2003 | Niles et al. | |
| 7,063,669 B2 | 6/2006 | Brawner et al. | |
| 7,282,032 B2 * | 10/2007 | Miller | A61B 5/085 600/533 |
| 7,390,305 B2 | 6/2008 | Nuttall | |
| 7,625,345 B2 * | 12/2009 | Quinn | A61B 5/091 482/13 |
| 2004/0249300 A1 * | 12/2004 | Miller | A61B 5/085 600/532 |
| 2004/0260195 A1 | 12/2004 | Barrul | |
| 2005/0256421 A1 | 11/2005 | Bryant | |
| 2006/0100537 A1 | 5/2006 | Williams et al. | |
| 2006/0206036 A1 * | 9/2006 | Quinn | A61B 5/087 600/538 |
| 2006/0282002 A1 * | 12/2006 | Wang | A61B 5/0876 600/538 |
| 2007/0043302 A1 * | 2/2007 | Masuo | A61B 5/0537 600/547 |
| 2007/0239058 A1 | 10/2007 | Krasilchikov et al. | |
| 2008/0000477 A1 | 1/2008 | Huster et al. | |
| 2008/0249429 A1 * | 10/2008 | Garbe | A61B 5/09 600/539 |
| 2009/0156952 A1 | 6/2009 | Hunter et al. | |
| 2009/0184968 A1 * | 7/2009 | Boschetti Sacco | A61B 5/087 345/473 |
| 2009/0270751 A1 | 10/2009 | Peng et al. | |
| 2010/0121211 A1 | 5/2010 | Bryant et al. | |
| 2011/0021940 A1 * | 1/2011 | Chu | A61B 5/08 600/529 |

* cited by examiner

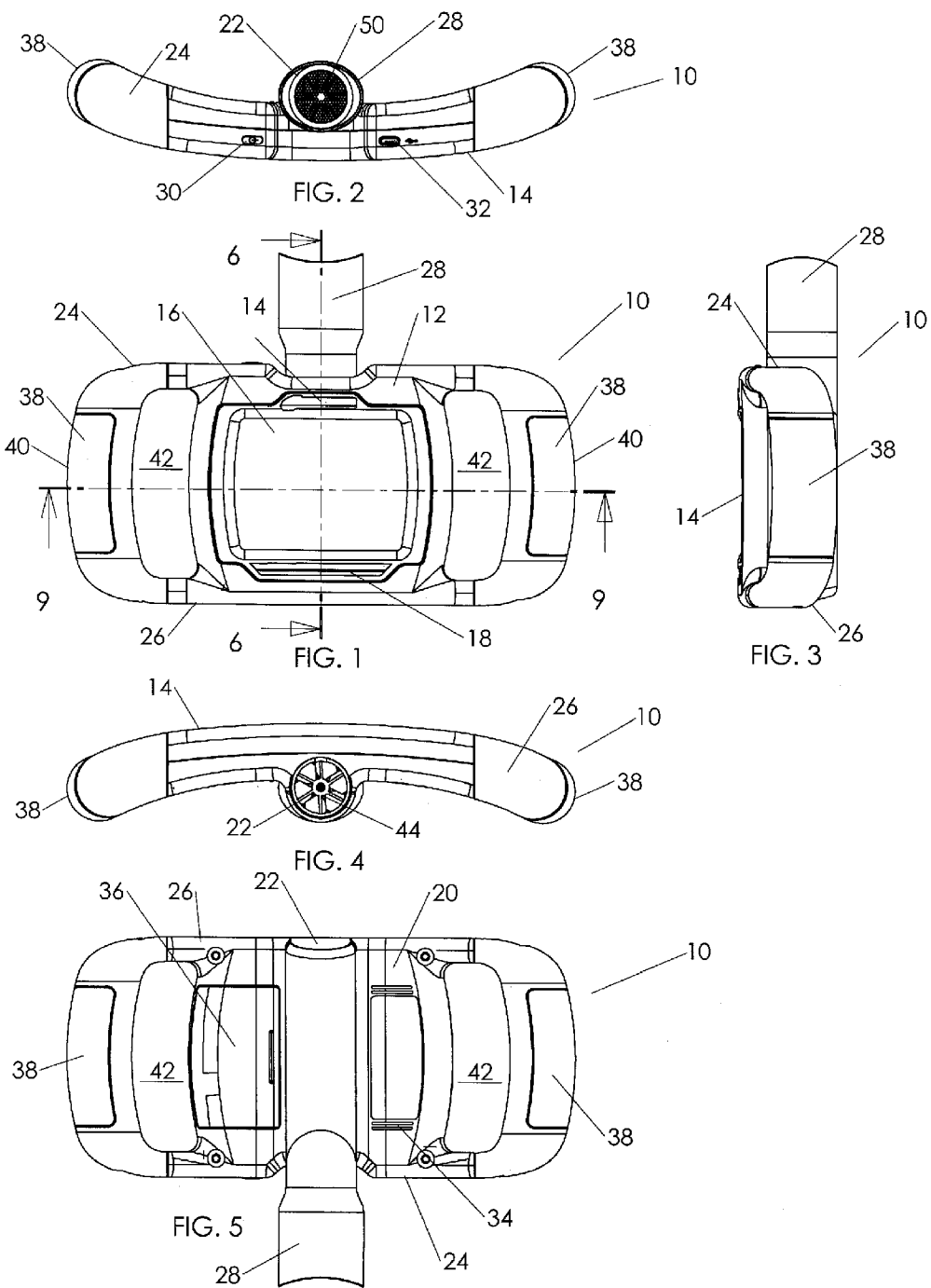

PERSONAL SPIROMETER

BACKGROUND OF THE INVENTION

The present invention relates to a spirometer or like respiratory testing device for use in testing lung and airway capacity or function of a patient and/or for measuring the amount or volume and/or speed or flow of air that can be inhaled and/or exhaled by the patient, and more particularly, the present invention relates to a portable, lightweight, hand-held spirometer particularly suitable for home and personal use, although equally capable of being used in hospitals, doctor's offices, and like institutions. The present invention is also directed to a system, software, and method for obtaining, storing and displaying the results of spirometry tests.

In general, a spirometry test measures the air entering and leaving the lungs and airways and is often used as a preliminary test for accessing the health condition of a patient's lungs and airways as well as a means for periodically tracking the progress of disease treatment and effect of medication. The spirometry test is typically performed using a device known as a spirometer, and the data provided by the test is often provided graphically in the form of a "volume-time curve" in which volume in liters is shown along the Y-axis and time in seconds is shown along the X-axis and/or in the form of a "flow-volume loop" in which the rate of airflow is shown on the Y-axis and the total volume inspired or expired is shown on the X-axis.

By way of example, a few common parameters that may be measured during respiratory testing include: Forced Vital Capacity (FVC) which is the total volume of air that can be forcibly blown out after full inspiration; Forced Expiratory Volume (FEV) at timed intervals (for instance, at 1.0 second (FEV1)); Forced Expiratory Flow (FEF) which is the average flow (speed) of air coming out of the lungs and airways during a specified period of the expiration; and Peak Expiratory Flow (PEF) which is the maximum flow (speed) of air during maximum expiration initiated after full inspiration. These parameters are often provided in raw data form (i.e., in liters, liters/second, liters/minute, etc.) and as percent predicted (i.e., a percent of a predicted value for a patient of similar age, height, weight, gender and ethnicity).

Each test is typically repeated three times to ensure reproducibility. The obtained results of the tests are highly dependent on patient cooperation and effort. For meaningful and valid test results to be obtained, the patient must provide vigorous and maximum respiratory effort for full expiration and/or inhalation. Typically, if the test is given during an office visit or at a hospital or the like, the patient will be coached and motivated by the attending nurse, physician or technician to keep exhaling as hard as possible for a predetermined period of time (i.e. "keep going, don't stop"). However, no such assistance is typically provided during home use of a spirometer; thus, the obtained home test results may not necessarily be valid if maximum effort is not provided throughout the duration of full expiration or inhalation.

Some basic examples of spirometers and like instruments are disclosed by U.S. Patent Application Publication Nos. 2006/0282002 A1 of Wang et al., 2007/0239058 A1 of Krasilchikov et al., 2009/0270751 A1 of Peng et al., 2006/0100537 A1 of Williams et al. and 2005/0256421 A1 of Bryant et al. and by U.S. Pat. No. 5,518,002 issued to Wolf et al., U.S. Pat. No. 5,816,246 issued to Mirza, U.S. Pat. No. 6,447,459 B1 issued to Larom, U.S. Pat. No. 7,282,032 B2 issued to Miller, U.S. Pat. No. 4,122,842 issued to Pikul, D.339,635 issued to Waterson et al., U.S. Pat. No. 7,390,305 B2 issued to Nuttall, U.S. Pat. Nos. 6,019,731 and 6,042,551 issued to Harbrecht et al., U.S. Pat. No. 4,736,750 issued to Valdespino et al., U.S. Pat. No. 4,991,591 issued to Jones et al., U.S. Pat. Nos. 5,715,831 and 6,113,549 issued to Johnson, U.S. Pat. No. 6,176,833 B1 issued to Thomson, U.S. Pat. No. 4,635,647 issued to Choksi, U.S. Pat. No. 4,495,944 issued to Brisson et al., U.S. Pat. No. 6,238,353 issued to Weinstein et al., U.S. Pat. No. 6,656,129 B2 issued to Niles et al. and U.S. Pat. No. 7,625,345 B2 issued to Quinn.

While known spirometers and like respiratory testing instruments may function in an acceptable manner, there continues to be a need for a portable personal spirometer having improved features with respect to ease of use and ability to readily and reproducibly obtain meaningful, valid test results so that progress of treatment and effect of medication over an extended period of time can be tracked in a reliable manner. For instance, a spirometer that is lightweight and compact and enables unsupervised use of the spirometer at home or the like yet still generates meaningful, reliable and valid test results that can be saved and studied at a later time by a patient, nurse, doctor or physician is desired.

SUMMARY OF THE INVENTION

According to one aspect of the present invention, a portable, hand-held spirometer is provided having a casework housing with front and rear panels, proximal and distal ends, and opposite side edges. An opposed pair of handgrips are formed by the housing at the opposite side edges, and a pair of finger-receiving throughholes extend through the housing adjacent each of the handgrips. This configuration permits each of the handgrips to be gripped by a hand of a user such that the hand of the user is able to fully encircle, extend around, and gird the handgrip enabling tight gripping and squeezing of the handgrips. The spirometer also includes an air flow tube extending underneath the front panel across the housing from the proximal end to the distal end and a mouthpiece connected to the air flow tube. The air flow tube is located centrally between the opposed pair of handgrips and is spaced from each of the handgrips.

According to contemplated embodiments of the spirometer, each of the air flow tube and handgrips is elongate and has a central longitudinally-extending axis, and the central longitudinally-extending axis of the air flow tube is substantially coplanar with the central longitudinally-extending axes of the handgrips. In addition, the central longitudinally-extending axis of the air flow tube and the central longitudinally-extending axes of the handgrips can be substantially parallel. Further, each of the handgrips can include an outer covering of an elastically-deformable, squeezable material.

The spirometer can also include an electronic display screen mounted on the front panel above the air flow tube and between the pair of finger-receiving throughholes. This display screen can be a color touch screen LCD display. Thus, data entry and user control of the spirometer is provided by touching icons, test listings, or other selections displayed on the screen. In addition, a color display enables test results and graphs to be color-coded thereby permitting results considered of "high" severity to be clearly highlighted on the display.

The spirometer can further include an accumulated volume indicator on the front panel of the housing in a position conveniently viewable by the user when taking a respiratory test. The indicator progressively becomes illuminated along its length during a respiratory test based on an amount of accumulated volume of air passing through the air flow tube measured in real-time by the spirometer. The indicator becomes fully illuminated when the accumulated volume of air measured in real-time by the spirometer equals a Predicted Forced Vital Capacity (PFVC) or a Predicted Inspiratory Vital Capacity (PIVC) specifically determined for the particular user. A microprocessor can be mounted within the housing to receive information concerning the flow of air through the air flow tube during a respiratory test and can determine values for PFVC or PIVC based on stored information of the user's age, gender, height, weight and ethnicity. In addition, the microprocessor controls illumination of the indicator based on a calculated percentage of the PFVC or PIVC reached by the accumulated volume of air measured in real-time by the spirometer during a respiratory test.

The spirometer can include a turbine assembly within the air flow tube. The turbine assembly includes a vane mounted for spinning rotation in the air flow tube. The vane is caused to rotate by air flow through the air flow tube, and a speed of rotation of the vane corresponds to a speed of air flow through the air flow tube at any instance in time. A pair of sensors can be arranged on opposite sides of the air flow tube adjacent the vane. One of the pair of sensors is a transmitter for directing a beam of electromagnetic radiation transversely across and through the air flow tube such that the beam is interruptible by rotation of the vane. The opposed sensor is a receiver for detecting whether or not the beam passes by the vane or is interrupted by the spinning vane at any point in time. The receiver generates and outputs an electronic digital signal to the microprocessor, and the signal corresponds to when the beam was received and when the beam was interrupted throughout duration of a respiratory test. As an example, the transmitter can be a diode, the receiver can be a phototransistor, and the electromagnetic radiation can be infrared radiation. A shroud can be extended in front of each of the sensors (receiver and transmitter). The shrouds can include narrow openings for the purpose of limiting the beam of infrared radiation being transmitted to a narrow spherical cone with a predetermined effective angle and for the purpose of limiting the infrared radiation being received to prevent any effects from undesired reflections within the air flow tube.

According to another aspect of the present invention, a method of receiving, processing and displaying information on a portable, hand-held spirometer is provided. Information concerning the age, gender, height, weight and ethnicity of a user is entered and stored on a microcontroller unit contained within the spirometer with data entry being via a color touch-screen display of the spirometer. Alarms/events are scheduled and stored in the microcontroller unit with data entry via the color touch-screen display with respect to date and time of day when respiratory tests are required to be taken by the user and when medications should be taken by the user. The microcontroller unit automatically causes the spirometer to issue alarms to remind the user of scheduled respiratory tests and times to take medication. These alarms can include both visual displays on the touch screen and audible sounds. Air flow through an air flow tube of the spirometer is measured in real-time during a respiratory test and an electronic digital signal is generated by sensors and forwarded to the microcontroller unit with respect to measured air flow. The microcontroller calculates and stores values of different test parameters measured and/or calculated from the respiratory test results and displays information concerning test results and/or test result trends in numerical data form and graphical form to the user via the color touch screen display. The particular test parameters, test results, test result trends, and display format is selectable by the user via use of the touch screen display.

Preferably, the method includes displaying a home page display on the touch screen display. The home page includes a plurality of icons that, when activated by being touched by the user, activate a function of the spirometer. Examples of functions include uploading data to a host computer, running a respiratory test, viewing test result trends, managing medications, and setting alarms.

The microcontroller unit determines predicted values of the test parameters based on the stored information of the user's age, gender, height, weight and ethnicity, determines and displays a percentage of the predicted value for each test parameter measured, and determines and displays a severity of each test parameter measured. In addition, when test results are displayed on the touch screen display, the test results are color-coded such that any test result determined to be of high severity by the microcontroller unit is automatically displayed in red or in flashing red to alert the user of the high severity of the test result.

BRIEF DESCRIPTION OF THE DRAWINGS

The features of the present invention should become apparent from the following description when taken in conjunction with the accompanying drawings, in which:

FIG. 1 is a plan view showing a front panel a spirometer according to the present invention;

FIG. 2 is an elevational view of a proximal, top, mouth-piece end of the spirometer of FIG. 1;

FIG. 3 is a side elevational view of the spirometer of FIG. 1;

FIG. 4 is an elevational view of a distal, bottom end of the spirometer of FIG. 1 opposite the mouth-piece end;

FIG. 5 is a view of the rear panel of the spirometer of FIG. 1 opposite the front panel;

DETAILED DESCRIPTION OF THE INVENTION

Figure 6:
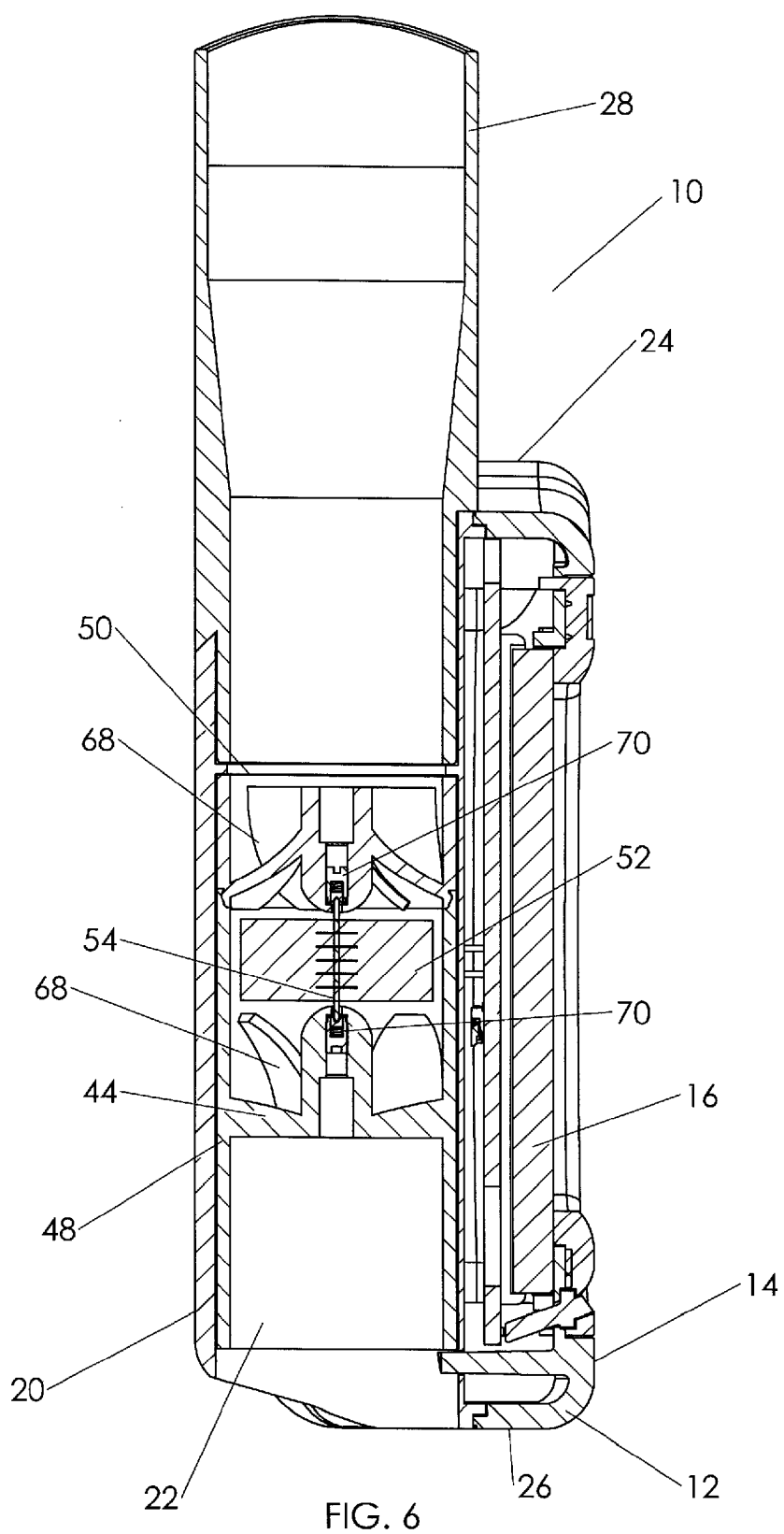
FIG. 6 is a cross-sectional view along line 6-6 of FIG. 1.

The basic exterior structure of a spirometer 10 according to the present invention is best illustrated in FIGS. 1-5. From the drawings, the spirometer 10 can have a relatively thin, elongate, rectangular casework or housing 12 that can be made, for instance, of plastic, metal, composite material, or the like. Of course, other shapes and materials for the casework housing 12 can be utilized. The illustrated embodiment is designed such that it is portable, lightweight and compact and provides a hand-held, battery-powered device suitable for home or personal use, although not limited to such use. The overall size of the spirometer 10 is such that it can be readily stored in a handbag, drawer or the like and/or can be carried and taken with the patient as needed.

The front panel 14 of the spirometer includes a display screen 16 and can also have a coaching mechanism/indicator 18, and the rear panel 20 defines the location of an air flow tube 22 that extends at a central location across the spirometer 10 from a proximal top end 24 to a distal bottom end 26. A mouthpiece 28 is located on the end of the air flow tube 22 and extends forward of the proximal top end 24 of the spirometer 10. The mouthpiece 28 can be made of transparent material for ease of cleaning and have an ergonomic design that provides comfort during use. The spirometer 10 can also include a power button 30 and a connection port 32, such as a micro USB port, on the proximal top end 22 and a speaker/grill 34 and removable battery compartment panel door 36 on the rear panel 20. The batteries (not shown) can be rechargeable, and the spirometer 10 can also be powered via use of an AC power adaptor.

The casework housing 12 includes a pair of oppositely located handgrips 38 that extend on opposite sides 40 of the spirometer 10 and that form the side edges of the spirometer 10. In addition, the casework housing 12 includes a finger-receiving throughhole 42 adjacent each handgrip 34. Each throughhole 42 permits the fingers of the person gripping the spirometer 10 to extend completely around the handgrips 38 such that each handgrip 38 can be tightly gripped and squeezed in the hand of the user. As best illustrated in FIG. 5, each handgrip 38 is generally elongate and extends substantially along and in the same direction/orientation as the air flow tube 22, and each handgrip 38 can be equally spaced from the centrally located air flow tube 22. Also, as best illustrated in FIG. 3, the central longitudinally-extending axis of each of the handgrips 38 and the central longitudinally-extending axis of the air flow tube 22 are essentially aligned and coplanar (i.e., extend substantially within the same imaginary plane). According to one contemplated embodiment, the outer surface layer of each handgrip 38 is textured to provide a non-slip surface and is made of rubber, an elastomeric material, or the like that is at least slightly deformable and elastic such that the handgrips 38 can be squeezed in the grip of the user.

Figure 16:
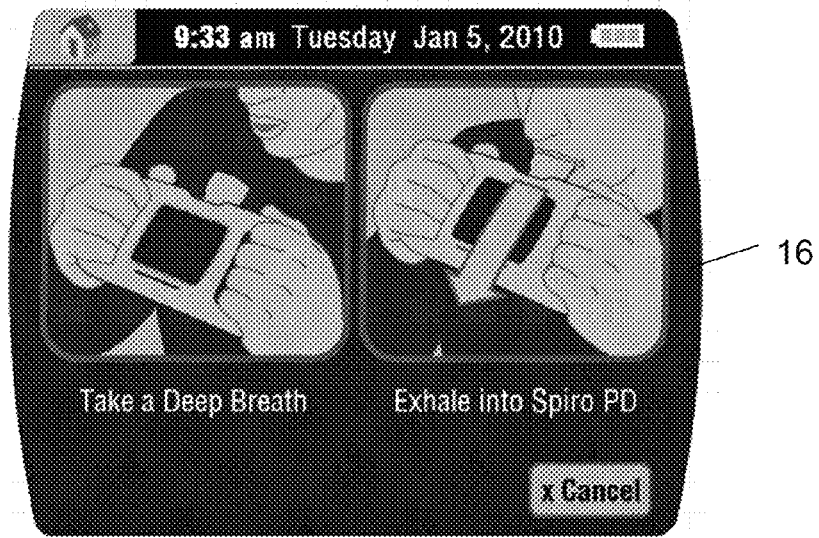
FIG. 16 is a screen shot image provided by the display screen of the spirometer of FIG. 1 providing visual instructions with respect to using the device.
Figure 18:
FIG. 18 is a screen shot image provided by the display screen of the spirometer of FIG. 1 providing an illustration of a person in proper position for taking a test.

The configuration of the handgrips 38 of the spirometer 10 provides an important function in properly positioning the user to ensure maximize respiratory effort and results during a respiratory test. In use, preferably the user sits or stands with their back in a generally upright position and with shoulders arched backward (i.e., not in a slumped forward position) with good posture. The user grips the spirometer 10 tightly with both hands as best illustrated in FIGS. 16 and 18. Thus, one hand of the user grips one of the handgrips 38 with the fingers of the user extending completely through the adjacent throughhole 42 such that user's hand completely encircles and girds the handgrip 38, and the other hand of the user grips the other handgrip 38 with the fingers of the user extending completely through the adjacent throughhole 36 such that user's hand completely encircles and girds the handgrip 38. In this position, the shoulders of the user are flexed backward and the arms of the user extend laterally and generally horizontally with bent elbows of the user pointing laterally and outward. In this balanced and proper posture position, the chest of the user is generally "open" and ready for maximize inhalation and/or exhalation.

Thus, for example, the user takes a deep breath while in the above described position, places his/her mouth about the mouthpiece 28, and exhales into the air flow tube 22 of the spirometer 10 as hard as possible for as long as possible to generate meaningful and valid test results which are measured and stored by the spirometer 10. The spacing and angle between the opposite handgrips 38 and the position of the handgrips 38 relative to the air flow tube 22 of the spirometer 10 ensure maximum thoracic cage compactness of the user so that maximum effort can be applied and meaningful results can readily be obtained in a reproducible manner. Thus, the above referenced configuration of the handgrips 38 and spirometer 10 optimizes user position and posture so that the best test results and readings can be obtained according to the best human factors.

In addition, the handgrips 38 can be made of a squeezable/elastically deformable material that provides a squeezing sensation to the user when tightly gripped enhancing the ability of the user to tighten the muscles in their arms, shoulders and back so that a deep breath can be taken before fully exhaling into the spirometer 10 or so that the user can fully inhale through the air flow tube. All of the above induces the strongest breathing possible by the patient to ensure meaningful and valid results are obtained in a reproducible manner.

Another aspect of the spirometer 10 of the present invention is that it includes a mechanism that provides real-time, automatic coaching and assistance to the user with respect to the expected duration of full expiration and/or inhalation. Thus, this mechanism provides a further means to ensure that the best possible test results are obtained by providing meaningful information to the user in real-time, for instance, while the user is exhaling into the spirometer 10 during a test. More specifically, the spirometer 10 includes the coaching mechanism/indicator 18 on the front panel 14 which is in full view by the user as the user is exhaling into the spirometer 10 or inhaling through the spirometer 10.

According to one contemplated embodiment, the indicator 18 is in the form of an elongate continuous or discontinuous line or sequence of light such as provided, for instance, by a light pipe, a series or array of light-emitting diodes (LEDs), or like visual indicator. Other visual effects can also be used such as images or the like, and the display screen 16 can be used for this purpose. An audible indicator (such as sounds emitted from the speaker/grill 34) can be used simultaneously in conjunction with the visual indicator 18 or in place of the visual indicator 18 for providing the same general purpose.

The visual indicator 18 can be specifically used to reflect the expected Force Vital Capacity (FVC) (i.e., the total volume of air that can be forcibly blown out after full inspiration) of the patient or the expected Inspiratory Vital Capacity (IVC) (i.e., the total volume of air that can be inhaled after full exhalation). For instance, the user's age, height, weight, gender and ethnicity are entered into the spirometer 10 via use of the display screen 16, which for example can be a color touch-screen LCD display, and these entries can be stored in a microprocessor and/or other electronic memory provided within the spirometer 10. Alternatively, these data entries can be input into the spirometer 10 via an external computer connected to the spirometer 10 via the connection port 32, which can be a micro USB port. From this information, the microprocessor of the spirometer 10 calculates a Predicted Force Vital Capacity (PFVC) and/or a Predicted Inspiratory Vital Capacity (PIVC) expected for a person of the age, height, weight, gender and ethnicity entered and sets this as the value required to fully light the visual indicator 18 thereby providing an indication to the user in real-time of the duration of exhalation or inhalation sufficient to generate valid test results.

Figure 7:
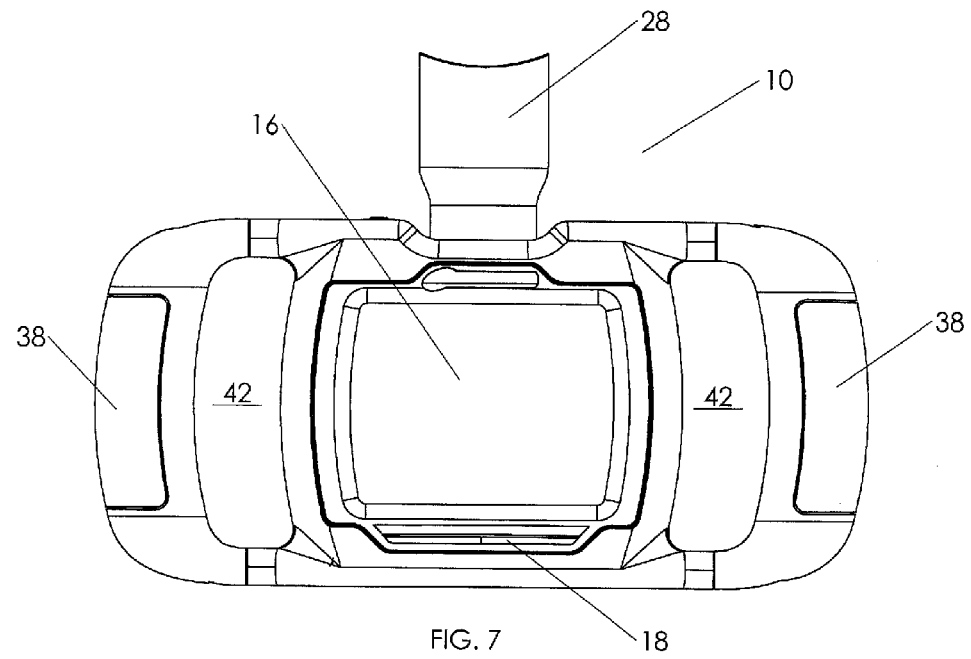
FIG. 7 is a plan view of the spirometer of FIG. 1 in which the coaching mechanism on the front display face is off or in an initial condition.
Figure 8:
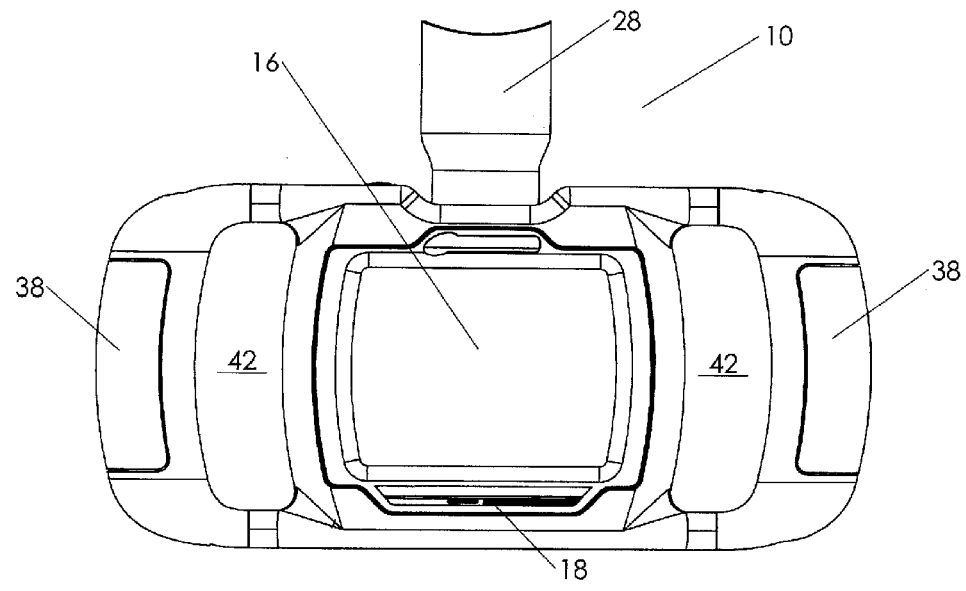
FIG. 8 is a plan view of the spirometer of FIG. 1 in which the coaching mechanism on the front display face shows progression during an Exhalation Mode or an Inhalation Mode.
Figure 9:
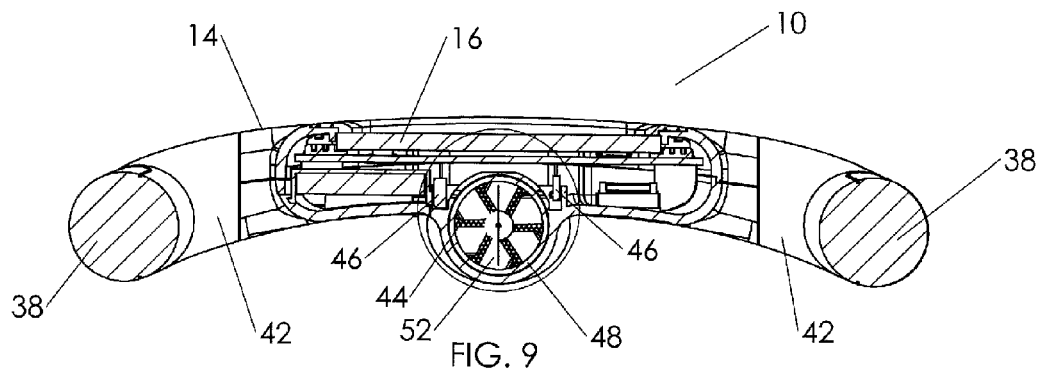
FIG. 9 is a cross-sectional view along line 9-9 of FIG. 1.

In use, before a user exhales (or inhales) into the spirometer 10, the elongate visual indicator 18 is completely unlit or "off" as best illustrated in FIG. 7. However, as the user begins exhaling (or inhaling) into the air flow tube 22 of the spirometer 10, the total volume of air flowing through the tube is continuously measured in real-time during the test, and the proportion of the Predicted Force Vital Capacity (or Predicted Inspiratory Vital Capacity) measured based on the real-time calculation is determined and reflected in the extent to which the visual indicator 18 is lit or "on". Thus, one end of the visual indicator 18 will become lit, and as the user continues to exhale (or inhale) into the spirometer 10, progressively more of the visual indicator 18 will light-up as best shown in FIG. 8, until the entire indicator 18 is lit or "on". In this manner, the indicator 18 coaches and provides incentive to the user to continue to exhale (or inhale) into the air flow tube 22 at least until the full length or a predetermined length of the visual indicator 18 is lit which reflects the predicted volume of air expected during full exhalation (or full inhalation) by the particular patient. Thus, the patient is coached to "don't stop, keep going" by the coaching mechanism 18 and the user can view the indicator 18 during a test so that meaningful and reproducible results can be obtained.

According to one contemplated embodiment, the spirometer 10 of the present invention measures the flow of air through the air flow tube 22 with a turbine assembly 44 and at least a pair of oppositely located rotation-detecting sensors 46. The air flow tube 22 and turbine assembly 44 are best illustrated in FIG. 6.

The air flow tube 22 generally includes the mouthpiece 28 and a turbine tube 48 which are connected end-to-end by the housing 12 with a mesh protective screen 50 or the like provided therebetween. The mesh screen 50 prevents foreign objects from entering and possibly damaging the turbine assembly. The mouthpiece 28 can be removable from the spirometer 10 for cleaning and/or replacement purposes.

A vane 52 is mounted for rotation on a spindle 54 within the turbine tube 48 between a series of stationary air flow deflectors 68. The opposite ends of the spindle 54 are positioned and ride within vee jewel assemblies 70 that enable the spindle 54 to rotate about its longitudinal axis within the turbine tube 48. The vee jewel assemblies 70 are high precision spring-loaded bushings that greatly reduce friction thereby permitting high revolutions per minute (RPMs) to be achieved by the vane 52 and spindle 54. Thus, when the user exhales (expires) or inhales (inspires) into/out of the air flow tube 22, the flow of air through the turbine tube 48 will cause the vane 52 and spindle 54 to rotate. The vane 52 will rotate faster when the speed of the air flow is greater, and the vane 52 will rotate slower when the speed of air flow decreases. In addition, the direction of rotation of the vane 52 and spindle 54 can be monitored to determine whether the patient is exhaling or inhaling into the spirometer 10.

The rotation of the vane 52 is monitored by the rotation-detecting sensors 46 mounted in opposite positions relative to the turbine tube 48. The sensors 46 are best illustrated in FIGS. 9-15. One of the sensors 46 can include a transmitter for transmitting a beam of visible or invisible light or electromagnetic radiation and a receiver for receiving/detecting the presence or absence of the beam at the receiver location. By way of example, the sensors 46 can include a diode for emitting a beam of infrared radiation or light (invisible to the human eye) and a photo-transistor that detects the presence or absence of the infrared light beam.

Figure 10:
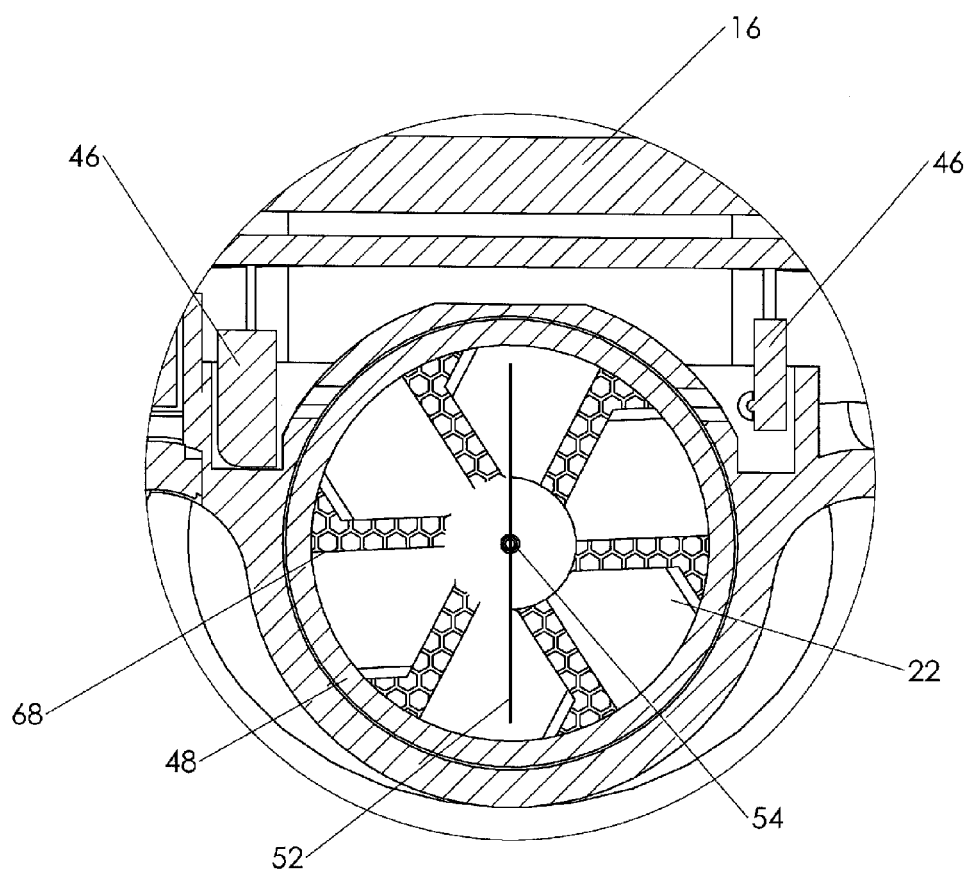
FIG. 10 is a magnified view showing a pair of turbine rotation sensors that detect rotation of a rotor within an air flow tube of the spirometer of FIG. 1.

As best illustrated in FIG. 10, the sensors 46 can be mounted at opposite positions about the turbine tube 48. In this position, a beam of infrared radiation or light, or some other beam of electromagnetic radiation, can be emitted transversely across and within the tube at the location of vane 52. In this manner, rotation of the vane 52 can interrupt the beam (see FIG. 11) or permit the beam to pass (see FIG. 12) depending upon the relative angular position of the rotating vane 52 at any instance of time.

The number of times the beam is interrupted by the vane 52 is equivalent to an accumulated angle of rotations of the vane 52, and therefore, the volume of air to pass through the turbine tube 48 can be readily determined since the dimensions of the turbine tube is known and since the speed of air flow is measured. The receiving sensor, such as a photo-transistor, produces a digital electrical output signal corresponding to the receipt of the beam and interruptions thereof. This digital signal is provided to the microprocessor or microcontroller within the spirometer 10 and can be used by the microprocessor or microcontroller to calculate, in real-time, the amount or volume of air flow during an inhalation or exhalation test. The flow can be measured on a timed basis, and the microprocessor can convert this information to an accumulated volume based on formulae in microcontroller firmware. For example, when the patient is exhaling into the spirometer 10, the accumulated volume measurement is equivalent to a measurement of Forced Vital Capacity (FVC), or when the patient is inhaling through the spirometer 10, the accumulated volume measurement is equivalent to a measurement of Inspiratory Vital Capacity (NC).

As discussed above, the spirometer 10 can already have calculated the Predicted Forced Vital Capacity (PFVC), and the microprocessor or microcontroller can divide the FVC measured at any instance of time in real-time by the PFVC to produce a percentage of PFVC used to progressively light the indicator 18 discussed above. Also, if the patient inspires (inhales) into the spirometer 10, an accumulated volume of air flow can be determined and provide a measure of Inspiratory Vital Capacity (IVC). The spirometer 10 can calculate a Predicted Inspiratory Vital Capacity (PIVC), and the microprocessor or microcontroller can divide the IVC measured at any instance of time in real-time by the PIVC to produce a percentage of PIVC used to progressively light the indicator 18 discussed above.

Figure 11:
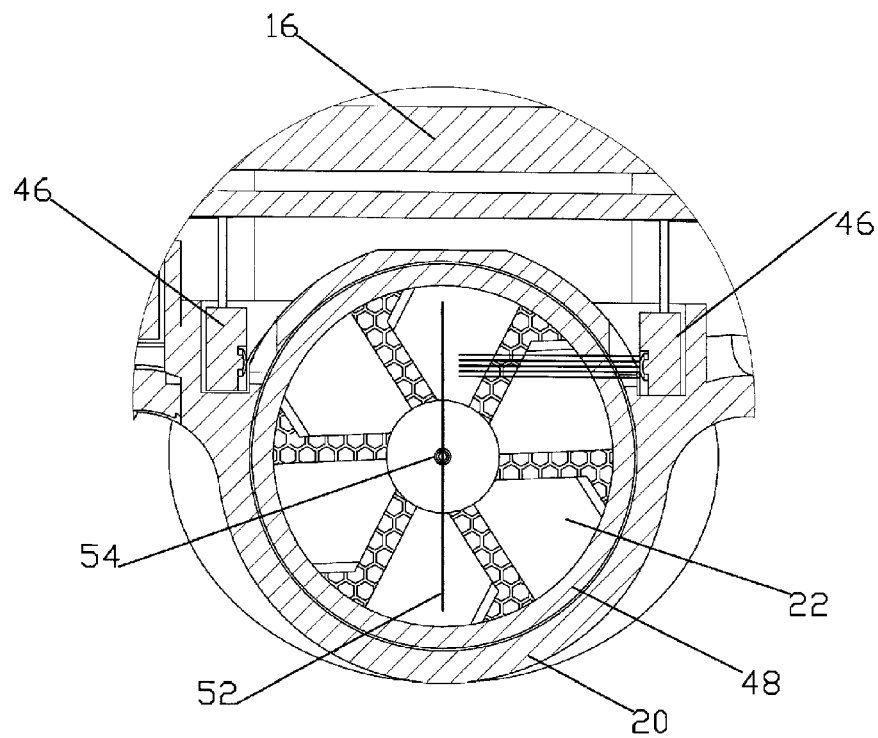
FIG. 11 is a view showing the pair of turbine rotation sensors of FIG. 10 in which a vane of the rotor blocks a beam of electromagnetic radiation, such as a beam of infrared radiation, from being received by a receiving sensor.
Figure 12:
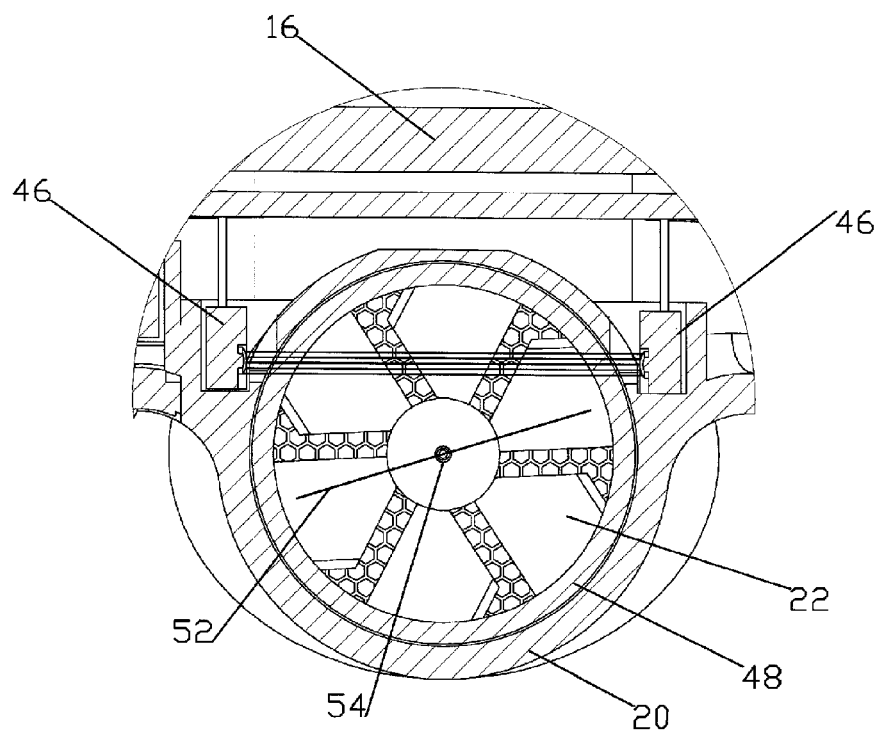
FIG. 12 is a view showing the pair of turbine rotation sensors of FIG. 10 in which the beam of electromagnetic radiation, such as a beam of infrared radiation, passes by the vane of the rotor and is received by the receiving sensor.
Figure 13:
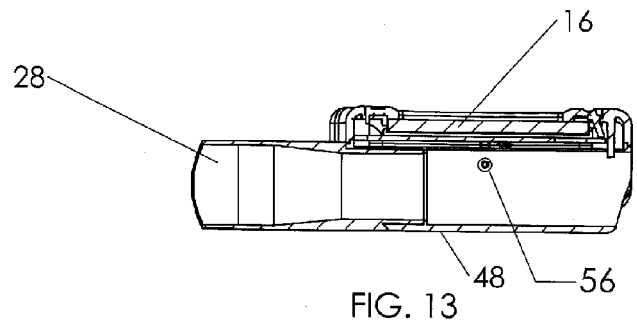
FIG. 13 is a cross-sectional view showing a restricted aperture provided in a wall of the air flow tube adjacent the receiving sensor.
Figure 14:
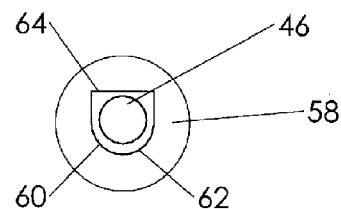
FIG. 14 is a magnified view of the restricted aperture and receiving sensor.
Figure 15:
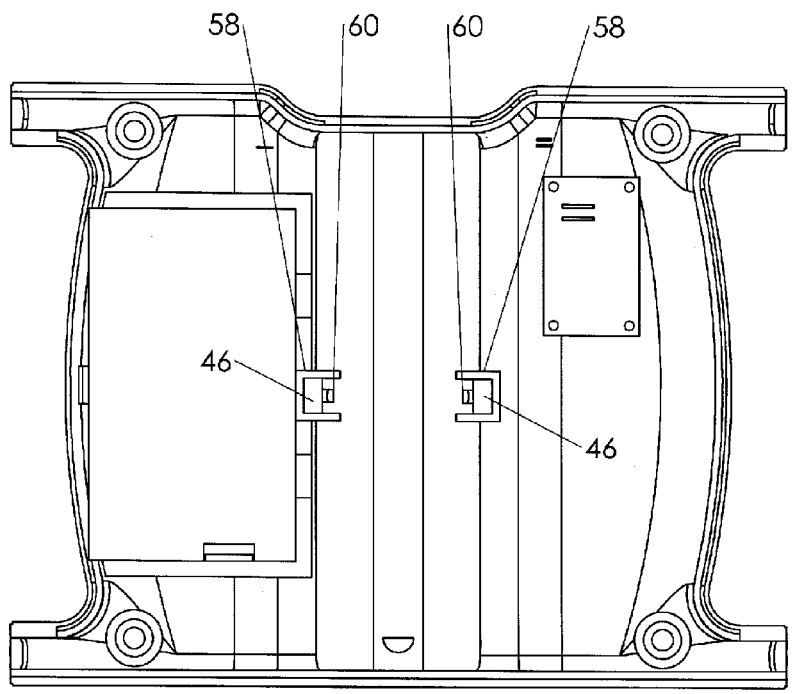
FIG. 15 is a view showing the pair of sensors positioned inside of the spirometer of FIG. 1.

As best illustrated in FIGS. 10-12, the sensors 46 are located external of the turbine tube 48 and apertures, such as aperture 56 best shown in FIG. 13, are formed in the wall the turbine tube 48. Infrared light emitted from a light emitting diode (LED), for example, typically does not form a narrow line beam along its full path; rather, it typically is emitted in the form of a spherical cone that expands, for instance, at about plus or minus 20°. Thus, as the light travels from the LED, the beam widens and expands forming a spherical cone-shaped beam. This wide angle often increases unwanted reflections within the surrounding enclosure, such as reflections off the walls of the turbine tube 48. Accordingly, a shroud 58 can be provided about each sensor 46 or at least in front of each sensor 46 and provide a narrow slit-shaped aperture 60 directly in front of each sensor 46 exterior of the turbine tube 48. The apertures 60 limit the angle and shape of the infrared light beam crossing the turbine tube 48 and limit the ability of a reflection from being received by the receiving sensor. Preferably, the widening of the beam as it extends from the LED is limited to a predetermined effective angle. Merely for purposes of example, the effective angle can be plus or minus 2°, or in a range of 1° to 5°, or any other angle or range of angles. Limiting the effected angle optimizes the light received by the receiving sensor when the receiving sensor is to properly receive the beam and further minimizes internal optical reflections at all times to prevent inaccurate readings caused by reflections. By way of example, the aperture 60 can have one end 62 formed as a semicircle of a radius of about 1 mm and an opposite squared-off end 64. See FIG. 14.

The operation of the spirometer 10 can be controlled by software, firmware or the like contained within the spirometer 10 via a microprocessor, microcontroller unit, or the like. Preferably, the display screen 16 is a touch screen used to display various icons or the like that can be touched to activate a specific function. Thus, the software receives the user's inputs via the touch screen and provides an appropriate response via displaying further information on the display screen 16.

By way of example, the spirometer 10 can normally display a home screen having a plurality of icons which can include, for instance, an upload data icon, a run test icon, a view trends icon, a manage medicines icon, and a set alarm icon. Any of these icons can be touched by the user to activate the corresponding programming of the spirometer. The home screen can also include a battery icon showing the status of charge of the rechargeable battery and a scrollable display of a list of upcoming scheduled events or alarms with respect to when respiratory tests are scheduled to be run and when medications are scheduled to be taken. Of course, the time, date and day of the week can also be displayed.

When it is time for a scheduled event or alarm, a pop-up screen appears on the touch screen display 16 and requests the patient to run a test, take a medicine, or dismiss the event/alarm. An audible alarm can simultaneously be generated to also remind the patient of the need to take a test or medicine. By way of example, if the user presses the run test icon in the pop-up screen or the home screen, the display screen 16 will appear as shown in FIG. 16. This provides instructions to the user with respect to the desired test. As shown in FIG. 16, the user is shown how to hold the spirometer and is instructed to take a deep breath and then exhale into the spirometer (or fully inhale through the spirometer depending on the test). Typically, the spirometer will require the user to take three identical tests and will instruct the user with respect to the additional tests. If any of the tests are incorrectly performed, the spirometer will provide instructions with respect to re-taking the test.

After a test is successfully completed, including all three test trials, the best test results of the trials will be displayed on the display screen 16 of the spirometer. By way of example, this may include values for FVC, FEV1, FEV1/FVS, FEF 25-75, and PEF. Of course, other or different values can be displayed depending upon the particular test taken, for example a value of IVC may be provided. The percentage of these test values relative to that predicted for the patient (i.e. based on age, gender, height, weight and ethnicity) can also be displayed on the screen. Further, the "severity" of each of these values can be listed (i.e. "high", "normal", "moderate", "mild", "low", "etc.). The user is also provided with additional icons with respect to uploading the data to an external host computer, viewing graphical results of the test, and viewing trend data which is a log of all test data taken to date or within a selected date range.

When the user presses the view trends icon on the touch screen display 16, the screen lists the results of all tests taken along with the time and date of each test and permits the user to scroll through the complete listing. The user can limit this listing to a particular date range, if desired. In addition, the user can limit the listing to any particular test value, such as those discussed above. Preferably, the display screen 16 is a color screen and any test result considered of a "high" severity is displayed in red or in flashing-red to draw quick attention to the particular result.

Figure 17:
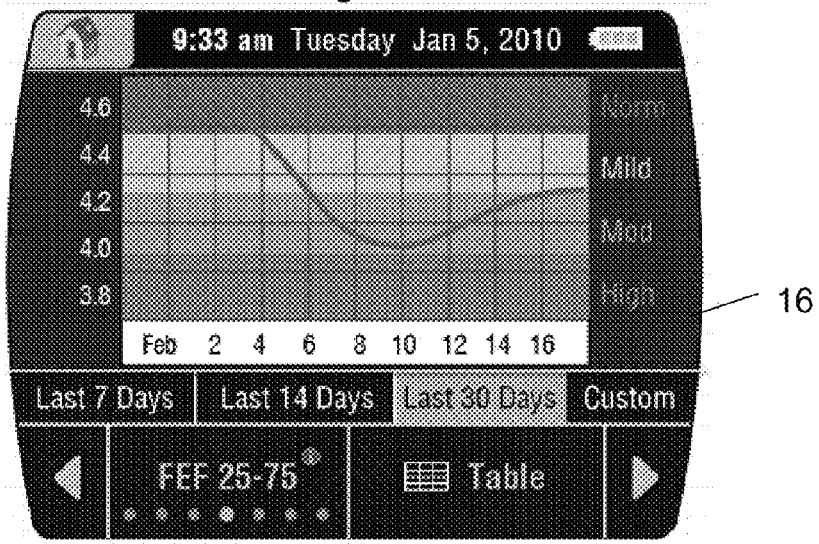
FIG. 17 is a screen shot image provided by the display screen of the spirometer of FIG. 1 providing an example of a display of graphical data.

The user can press the view graphical results for any particular test and for any particular value. For example, FIG. 17 shows the display screen 16 showing trend data for FEF 25-75 measurements. Since the display is a color display, the different parts of the graph are color-coded. For instance, the part of the graph representing "normal" can be color-coded green, the part of the graph representing "mild" severity can be color-coded light-green, the part of the graph representing "moderate" severity can be color-coded orange, and the part of the graph representing "high" severity can be color-coded red. For example, as shown in FIG. 16, the test results were initially normal, fell to "moderate" severity and more recently show "mild" severity.

The above style graph can be shown for any test or for any particular test values. In addition, the user can view flow-volume loops and volume-time curves for each test. Thus, the spirometer stores a number of tests and the test results can be viewed in numerical raw data format or in graphical format. By way of example, the spirometer can store up to 180 test results, 180 flow-volume loops, and 180 volume-time loops in internal memory. Of course, this memory can be increased to store a greater number of test results and the like.

When the user activates the manage medicines icon, the display screen provides a scrollable list of prescribed medicines along with the dosage and start and end dates. When the user selects a particular medicine, the scheduled times and dates to take the medicine is displayed. This screen also allows the user to enter a new medication to the list, check the medication schedule, view the medication history for medications already taken, and log an entry with respect to providing an acknowledgement that a medication was taken.

When the user activates the upload data icon, the display screen 16 provides instructions with respect to connecting a cable, such as a USB cable, to the connection port 32 of the spirometer 10 and to connect the cable to the external host computer. The particular data desired for upload can be selected and the data can be uploaded so that, for instance, the data can be viewed by a physician or the like.

In addition to the above, the device settings of the spirometer can be adjusted, such as, brightness of display, volume level/mute, time/daylight savings time, format of date, unit of measure (English, metric), language (English, Spanish, etc.), and font size of letters appearing in the display (large, small). The patient can also be initially prompted to enter their name, date of birth, gender, height, weight, and ethnicity and this information is saved in memory. Finally, the patient or caregiver can set up any number of alarms with respect to taking respiratory tests and/or medications at any desired time or times of day and for any days specified.

Accordingly, the user is provided with a tool that informs the patient with an alarm when to take respiratory tests and/or medications and instructions on how to take the tests. The structure of the spirometer ensures that reliable, valid and meaningful test results are taken, and all test results are electronically stored and can be viewed in numerous formats. Test results that are considered to be of "high" severity can be displayed in red or flashing red to draw quick attention to such results. The trends of the tests over a period of time can be viewed to see if the results are improving, staying the same, or becoming worse. Medication history of medicines taken can be viewed, and a schedule of medications to be taken can be viewed. All the above can be readily uploaded into a host computer, such as a computer of a physician, so that the physician can track the progress of treatment. Also, all operations of the spirometer can be controlled via selecting icons or the like on a touch screen color display panel.

While preferred spirometers, methods, systems and software have been described in detail, various modifications, alterations, and changes may be made without departing from the spirit and scope of the present invention as defined in the appended claims.

The invention claimed is:

1. A portable, hand-held personal spirometer, comprising:
   a curved front surface;
   a curved rear surface a distance from said front surface;
   wherein said front and rear surfaces define opposite ends, a proximal end, and a distal end;
   a pair of finger-receiving throughholes extending through said front and rear surfaces proximate said opposite ends, said throughholes being configured to permit passage of fingers of a user such that the fingers of the user are able to encircle, and grip portions of said front surface adjacent said throughholes;
   an air flow tube extending from said proximal end to said distal end, said air flow tube being located centrally between said opposed pair of throughholes;
   an electronic display screen on amid front surface; and
   a microprocessor disposed between said first and second surfaces and configured to receive information related to the flow of air through said air flow tube during a respiratory test, to determine a test value based, at least in part, on said information, and to cause representation of said value to be displayed on said display.

2. A portable, hand-held spirometer according to claim 1, wherein each of said air flow tube and said throughholes is elongate and has a central longitudinally-extending axis, and wherein said central longitudinally-extending axis of said air flow tube is coplanar with said central longitudinally-extending axes of said throughholes.

3. A portable, hand-held spirometer according to claim 2, wherein said central longitudinally-extending axis of said air flow tube and said central longitudinally-extending axes of said throughholes are parallel.

4. A portable, hand-held spirometer according to claim 3, further comprising handgrips adjacent said throughholes, each of said handgrips includes an outer covering of an elastically-deformable, squeezable material.

5. A portable, hand-held spirometer according to claim 1, wherein said electronic display screen is disposed on said front surface above said air flow tube and between said throughholes.

6. A portable, hand-held spirometer according to claim 5, wherein said display screen is a color touch screen LCD display.

7. A portable, hand-held spirometer according to claim 1, further comprising an accumulated volume indicator on said front surface in a position viewable by the user when taking a respiratory test, said indicator progressively becoming illuminated along its length during a respiratory test based on an amount of accumulated volume of air passing through said air flow tube measured in real-time by the spirometer such that said indicator becomes fully illuminated when the accumulated volume of air measured in real-time by the spirometer equals a Predicted Forced Vital Capacity (PFVC) or a Predicted Inspiratory Vital Capacity (PIVC) of the user.

8. A portable, hand-held spirometer according to claim 7, wherein said microprocessor determines values for said PFVC or PIVC based on information of the users age, gender, height, weight and ethnicity, and controls illumination of said indicator based on a calculated percentage of said PFVC or PIVC formed by the accumulated volume of air measured in real-time by the spirometer during a respiratory test.

9. A portable, hand-held spirometer according to claim 7, further comprising a speaker that provides an audible indication to the user during a respiratory test concerning the amount of accumulated volume of air passing through said air flow tube measured in real-time by the spirometer.

10. A portable, hand-held spirometer according to claim 1, further comprising a turbine assembly within said air flow tube, said turbine assembly including a vane mounted for spinning rotation in said air flow tube, said vane being caused to rotate by air flowing through said air flow tube and a speed of rotation of said vane corresponding to a speed of air flowing through said air flow tube at any instance in time.

11. A portable, hand-held spirometer according to claim 10, further comprising a pair of sensors arranged on opposite sides of said air flow tube adjacent said vane, one of said pair of sensors being a transmitter for directing a beam of electromagnetic radiation transversely across and through said air flow tube such that the beam is interruptible by rotation of said vane, and the other of said sensors being a receiver for detecting whether or not the beam passes by said vane at any point in time, said receiver generating and outputting an electronic digital signal corresponding to when the beam was received and when the beam was interrupted throughout a duration of a respiratory test.

12. A portable, hand-held spirometer according to claim 11, wherein said transmitter is a diode, said receiver is a phototransistor, and said electromagnetic radiation is infrared radiation.

13. A portable, hand-held spirometer according to claim 12, further comprising a shroud extending in front of each of said sensors and having a narrow opening limiting the beam of infrared radiation to a narrow spherical cone with a predetermined effective angle and limiting the receipt of reflections by the receiver.

14. The spirometer of claim 1, wherein said first and second surfaces are parallel.

15. A method of receiving, processing and displaying information on the portable, hand-held personal spirometer according to claim 1, comprising the steps of:
   storing information concerning the age, gender, height, weight and ethnicity of a user on the microcontroller contained within the spirometer with data entry via the electronic display screen of the spirometer, wherein the electronic display screen comprises a touch screen display;

scheduling and storing alarms in the microcontroller with data entry via the touch screen display with respect to date and time of day when respiratory tests should be taken by the user and when medications should be taken by the user;

automatically issuing alarms via the microcontroller from the spirometer to remind the user of scheduled respiratory tests and times to take medication;

measuring air flow through the air flow tube of the spirometer in real-time during a respiratory test and providing via sensors an electronic digital signal to the microcontroller with respect to measured air flow;

calculating and storing values within the microcontroller of different test parameters provided by respiratory test results; and displaying information concerning test results and test result trends in numerical data form and graphical form to the user via the touch screen display, wherein particular test parameters, test results, test result trends and display format are selectable by the user via use of the touch screen display.

16. A method according to claim 15, further comprising the step of displaying a home page display on the touch screen display having a plurality of icons that, when activated by being touched by the user, activate a function of the spirometer, the functions including uploading data to a host computer, running a respiratory test, viewing test result trends, managing medications, and setting alarms.

17. A method according to claim 15, wherein the microcontroller determines predicted values of the test parameters based on the stored information of the users age, gender, height, weight and ethnicity, determines and displays a percentage of the predicted value for each test parameter measured, and determines and displays a severity of each test parameter measured.

18. A method according to claim 17, wherein, when test results are displayed on the touch screen display, the test results are color-coded such that any test result determined to be of high severity by the microcontroller is automatically displayed in red or in flashing red to alert the user of the high severity of the test result.

19. A method according to claim 15, further comprising the step of managing medicines via the touch-screen display, including displaying a scrollable list of prescribed medicines along with dosage and start and end dates stored by the microcontroller, selecting a particular medicine on the display screen so that the microcontroller automatically displays scheduled times and dates to take the medicine, entering a new medication to the list of prescribed medicines, checking the medication schedule, viewing the medication history for medications already taken, and logging an entry with respect to providing an acknowledgement that a medication was taken.

20. A portable, hand-held personal spirometer, comprising:

a housing having front and rear sides proximal and distal ends and opposite side edges;

an opposed pair of handgrips at said opposite side edges, said handgrips being angled relative to each other, said handgrips being angled away from said front side;

wherein said housing is curved between said opposite side edges, and wherein said handgrips extend along the same curve;

a pair of finger-receiving throughholes extending through said housing adjacent each of said handgrips permitting each of said handgrips to be gripped by a hand of a user such that the hand of the user is able to encircle and grip said handgrip;

an air flow tube extending through said housing from said proximal end to said distal end, said air flow tube being located centrally between said opposed pair of handgrips.

* * * * *